(12) United States Patent
Bonner et al.

(10) Patent No.: US 6,479,296 B1
(45) Date of Patent: Nov. 12, 2002

(54) SOLID PHASE PRECIPITATION AND EXTRACTION

(76) Inventors: Alex G. Bonner, One Stimson Ave., Lexington, MA (US) 02173; Lawrence S. Udell, 114 Chestnut St., Brookline, MA (US) 02146; William A. Creasey, 19 Pine St., Bedford, MA (US) 01730; Stephen Duly, 30 River St., Andover, MA (US) 01810; Richard A. Laursen, 29 Howard Rd., #1, Newton, MA (US) 02458

( * ) Notice: Subject to any disclaimer, the term of this patent is extended or adjusted under 35 U.S.C. 154(b) by 0 days.

(21) Appl. No.: 09/610,761

(22) Filed: Jul. 6, 2000

Related U.S. Application Data

(60) Provisional application No. 60/142,582, filed on Jul. 7, 1999.

(51) Int. Cl.[7] ............................................. G01N 33/00
(52) U.S. Cl. .............................. 436/86; 436/85; 435/4
(58) Field of Search ............................. 435/4; 436/85, 436/86; 210/656

(56) References Cited

U.S. PATENT DOCUMENTS

| | | | | |
|---|---|---|---|---|
| 4,923,978 A | * | 5/1990 | McCormick | |
| 5,171,838 A | * | 12/1992 | Chiba | |
| 5,532,131 A | * | 7/1996 | Lewis | |
| 5,593,642 A | * | 1/1997 | DeWitt et al. | |
| 5,882,521 A | * | 3/1999 | Bouvier et al. | |

OTHER PUBLICATIONS

Albericio, F. et al., "Preparation and application of the 5–(4–(9–fluorenylmethyloxycarbonyl)–aminomethyl–3, 5–dimethoxyphenoxy)–valeric acid (PAL) handle for the solid–phase synthesis of c–terminal peptide amides under mild conditions," *J. Org. Chem.* 55:3730–43 (1990).

Baxter, A.D. "Autopurification of combinatorially derived compound libraries," *Genetic Engineering News*, 19:27 (1999).

Bonner, A.G. et al., Solid–phase precipitation and extraction, a new separation process applied to the isolation of synthetic peptides, *J. Peptide Res.*, 57:48–58 (2001).

Fields, G.B. et al., "Solid phase peptide synthesis utilizing 9–fluorenylmethoxycarbonyl amino acids," *Int. J. Peptide Protein Res.* 35:161–214 (1990).

Grace, R. et al., "Extractions can be painless—When you know how." *R&D Magazine* 51–54 (Aug. 1991).

King, D.S. et al., "A cleavage method which minimizes side reactions following Fmoc solid phase peptide synthesis," *Int. J. Peptide protein Res.*, 36:255–66 (1990).

Perkin Elmer, "Introduction to cleavage techniques," 2d ed. P. 1–19 (1990).

Simpson, N. "Solid–phase extraction: disposable chromatography," *American Laboratory* 37–43 (Aug. 1992).

Tippens, B. "Solid phase extraction fundamentals," *Nature*, 334:273–74 (Jul. 21, 1988).

Van Wandelen, C. et al., "Cleavage, deprotection, and isolation of peptides after Fmoc synthesis," Chemistry Update, Milligen/Biosearch, Division of Millipore; pp. i–iv, 1–17 (Dec. 1989).

Zuckerman, R.N. et al., "Automated peptide–resin deprotection/cleavage by a robotic workstation," *Peptide Research*, 5:169–174 (1992).

* cited by examiner

*Primary Examiner*—Ralph Gitomer
*Assistant Examiner*—Mahreen Chaudhry
(74) *Attorney, Agent, or Firm*—Lahive & Cockfield, LLP; Giulio A. DeConti, Jr., Esq.

(57) ABSTRACT

A new method, solid phase precipitation and extraction (SPPE), is disclosed and is particularly advantageous for purifying mixtures of synthetic peptides directly from a cleavage/deprotection mixture.

20 Claims, 10 Drawing Sheets

NOTE: Reagent L = trifluoroacetic acid 88%, dithiothreitol (DTT) 5%, water 5%, triisopropylsilane 2%)

NOTE: Reagent L = trifluoroacetic acid 88%, dithiothreitol (DTT) 5%, water 5%, triisopropylsilane 2%)

NOTE: Reagent L = trifluoroacetic acid 88%, dithiothreitol (DTT) 5%, water 5%, triisopropylsilane 2%)

NOTE: Reagent L = trifluoroacetic acid 88%, dithiothreitol (DTT) 5%, water 5%, triisopropylsilane 2%)

US 6,479,296 B1

SOLID PHASE PRECIPITATION AND EXTRACTION

RELATED APPLICATIONS

This application claims the benefit of priority under 35 U.S.C. 119(e) to copending U.S. Provisional Application No. 60/142,582, filed on Jul. 7, 1999, the entire contents of which are incorporated herein by reference. This application is related to copending U.S. application Ser. No(s). 09/287,076, filed on Apr. 6, 1999, the entire contents of which are incorporated herein by reference.

BACKGROUND OF THE INVENTION

Solid phase extraction (SPE) and liquid chromatography separations are well known, extensively used processes. Selective extraction, selective washing and selective elution are the three fundamentals of the SPE process and a stepwise procedure is used to separate compounds of interest from impurities. In the first step, the sorbent is conditioned with a solvent or eluent. In a second step, the sample is added and washed through the sorbent. Selected components are adsorbed when the sample passes through the SPE matrix and the effluent contains the non-adsorbed components. The third step involves selective washing with solvents that are strong enough to remove impurities but weak enough to leave compounds of interest behind. The final step is to wash the matrix with a solvent that will elute the compounds of interest. In some procedures, only two steps are necessary since the compounds of interest are collected in the effluent as the sample passes through the matrix with impurities remaining on the sorbent. These basic steps are typical for SPE using reverse phase, normal phase, and ion exchange sorbents.

SUMMARY OF THE INVENTION

The present invention relates to methods of isolating biological analytes such as synthetic peptides from a sample and are particularly advantageous for purifying mixtures of synthetic peptides directly from a cleavage/deprotection mixture. In an embodiment the invention relates to a method for isolating a biological analyte from a sample, comprising the steps of precipitating a biological analyte onto a solid phase extraction device; and eluting the biological analyte off of said solid phase extraction device. In an advantageous embodiment, the liquid sample is applied onto the solid phase extraction column followed by drying of said solid phase extraction device, preferably as a thin film on the solid phase extraction device, which can be, e.g., a packed column, a coated membrane or the like.

DETAILED DESCRIPTION OF THE INVENTION

The term "biological analyte" includes single analyte or a mixture thereof; preferably, e.g., proteins, peptides, nucleic acids and the like.

The term "solid phase extraction device" includes traditional solid phase extraction devices such as packed chromatographic columns, chromatographic preparatory devices, i.e., "short" cleanup columns, membranes, preferably having a solid phase to which the biological analyte can be deposited as a thin film, etc. The solid phase can be known phases such as reverse-phase, e.g., $C_8$ or $C_{18}$, ion-exchange, silica, etc.

Figure 15:
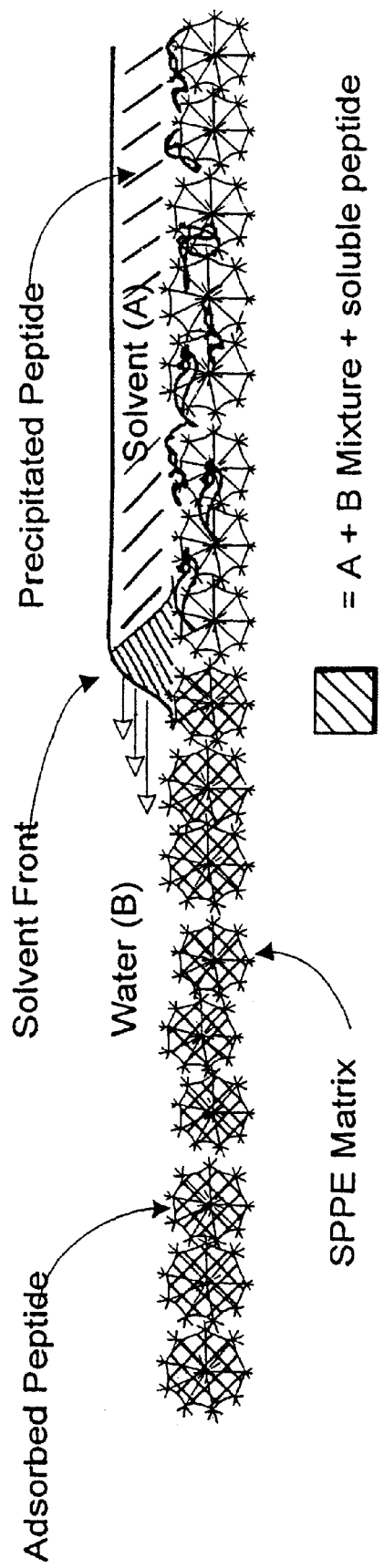
FIG. 15 is a graphical depiction of the "SPPE" process, wherein compounds of interest, in this case, peptides, are precipitated on the SPPE matrix by solvent (A) which simultaneously removes impurities and/or displaces water or the sample application solvent.

In the process of the present invention, a solid phase extraction device is used to (a) precipitate the compounds of interest onto the device and (b) leverage the large surface area thereof, e.g., a packed matrix, to support the precipitated compound of interest while impurities are washed away. The method, in effect, changes the sorbent into a support matrix for thin film deposition. In this manner, selected components or impurities can be solubilized completely and rinsed through or off the device with wash solutions that are (a) strong enough to remove the impurities, but (b) not the compounds of interest which are retained as a thin film precipitate on the surface, or in the pores of the sorbent. The precipitation step can be accomplished by various methods appropriate for the specific application. In one embodiment, vacuum may be used to strip solvent and cause precipitation on the sorbent. Alternatively, the compounds of interest can be precipitated after being adsorbed on the sorbent surface by the delivery of a stream of gas or by delivery of a wash solvent that will simultaneously exchange the initial wash solvent and cause the precipitation (in effect, a trituration step). FIG. 15 depicts the "SPPE" process, wherein compounds of interest, in this case, peptides, are precipitated on the SPPE matrix by solvent (A) which simultaneously removes impurities and/or displaces water or the sample application solvent.

Figure 1:
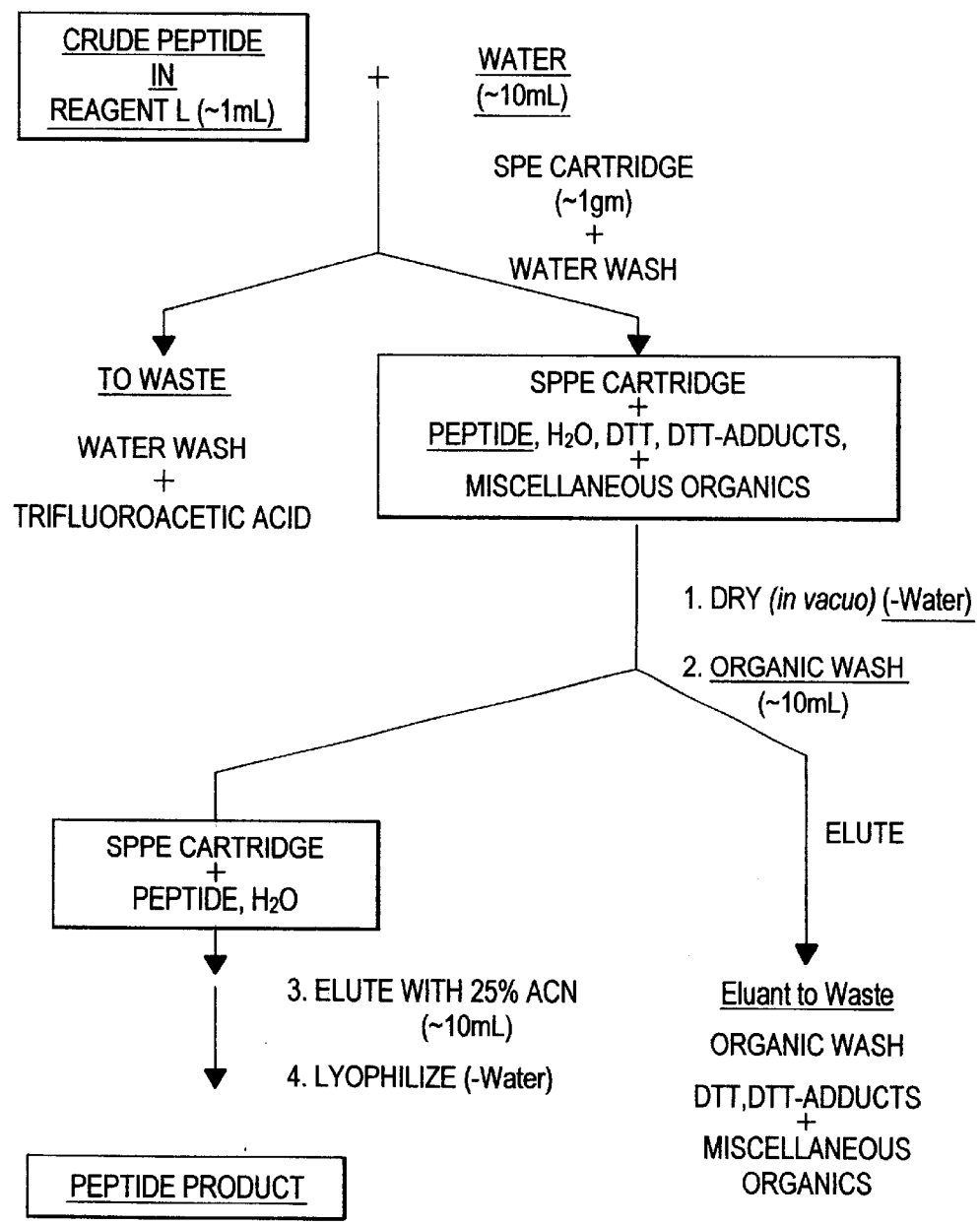
FIG. 1 schematically depicts an embodiment of a method of the invention in application to peptide synthesis chemistry.

As shown in FIG. 1, in application to peptide synthesis chemistry, in an illustrative embodiment the first step of the process the peptide components and impurities of the sample to the solid phase sorbent. In this example, the crude, synthetic peptide sample is adsorbed to a reverse phase solid support. The support is washed with water or trifluoroacetic acid ("TFA")/water. Salts and other impurities are washed through the column to waste. At this point, all components of the remaining sample mixture are partitioned between the solid phase sorbent and the residual solvent (water or TFA/water). However, the equilibrium is far to the side of the sorbent.

In the second step, a drying step is used to strip solvents (water, trifluoroacetic acid, and volatile organics) from the sorbent. After drying, there is no longer a partitioning system and the sample components are adsorbed to, or form a solid mixture with, the sorbent. This drying step causes the compounds of interest and the impurities to precipitate on the surface of the SPE particles. At this stage, the compound of interest and the impurities are in the solid form, supported on the surface or pores of the matrix.

In a third step, solvents are chosen, e.g., such that they can dissolve amino acid protective group derivatives or adducts, thiol scavengers, or other organic impurities which may have been carried along in the cleavage and deprotection chemistries, but not the desired peptide product. Selection of such solvents are within the skill of those in the art. With peptides or proteins as a desired biological analyte(s), such solvents as diethyl ether, dichloromethane, acetonitrile, acetone, or methanol may be used to wash through the column and carry away the impurities and leave the insolubilized/precipitated peptide trapped on the solid phase surface.

In a further step, a wash solvent is used to elute the compound of interest. This final wash solvent solubilizes the compound of interest under conditions which cause desorption from the matrix. Exemplary final wash solvents for reverse phase sorbents are acetonitrile/water (1:3) or acetic acid/water (1:3) which are chosen to solubilize the peptide, wash it away from the matrix, and allow for a final drying or lyophilization step.

Figure 2:
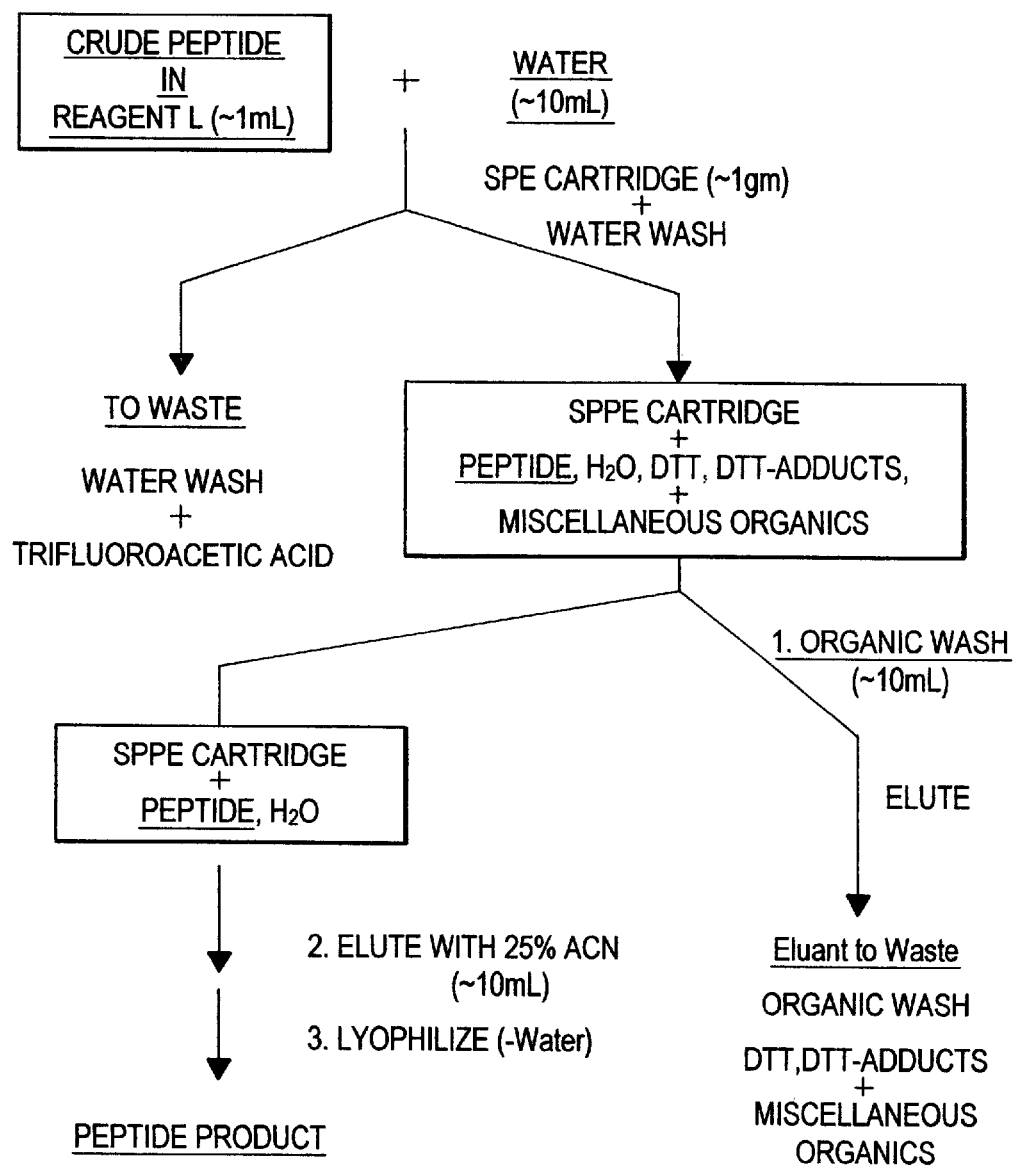
FIG. 2 schematically depicts an alternate embodiment of a method of the invention in application to peptide synthesis chemistry.

Alternatively, as shown in FIG. 2, the vacuum drying step may be eliminated from the process by the choice of appropriate wash solvents. After the sample is applied and adsorbed to the SPPE sorbent, water, trifluoroacetic acid, and impurities can be removed by delivering a wash solvent that will simultaneously (a) cause the compounds of interest to precipitate and deposit as a thin film, (b) solubilize the impurities and (c) displace the water. In this mode, the first traces of solvent (A) would mix with the water (B) causing dissolution of the peptide, but as the concentration of A is increased, the peptide precipitates and is trapped in or on the surface of the SPPE matrix.

Figure 3:
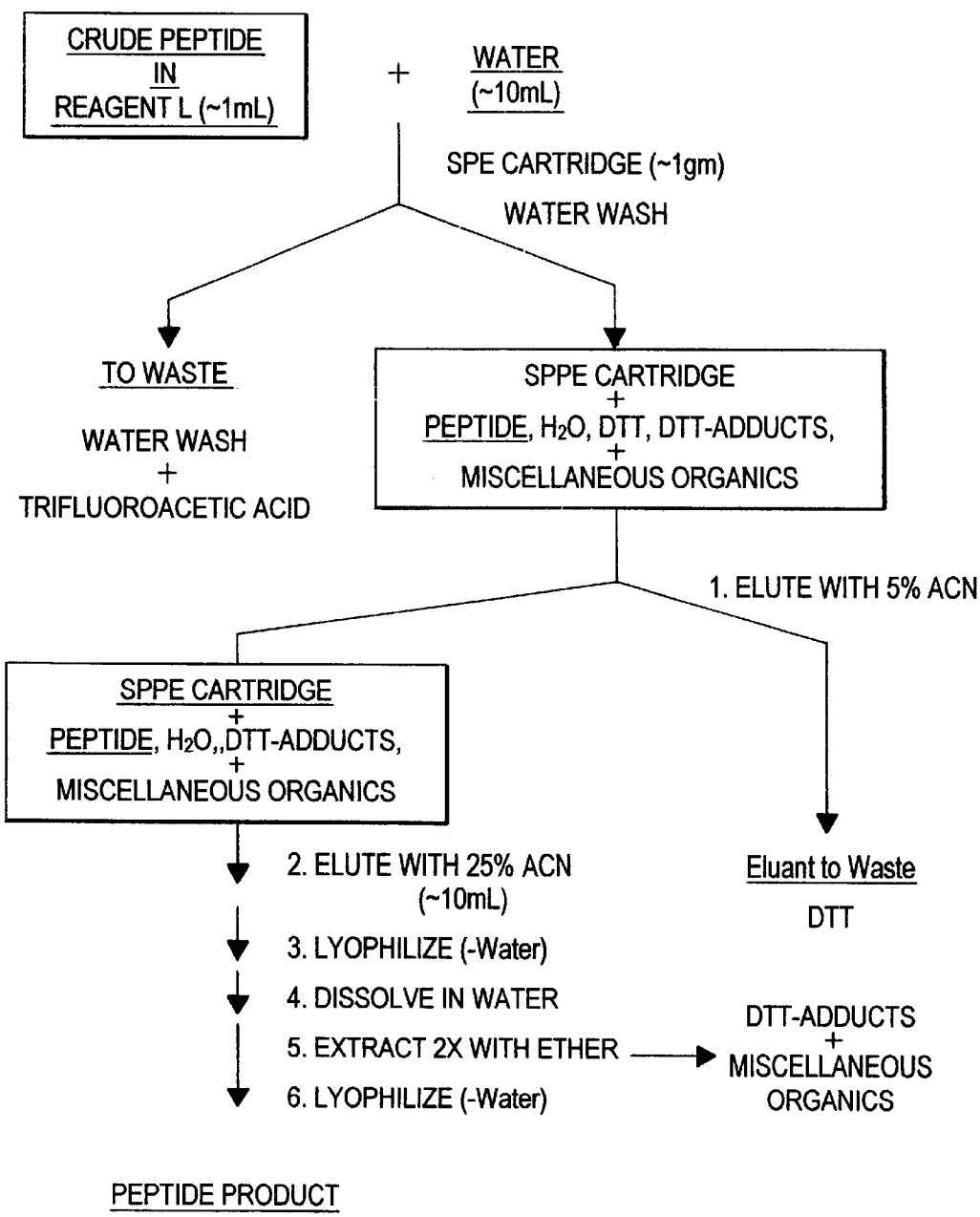
FIG. 3 schematically depicts, for comparison to the present invention, a prior art method for purification of synthetic peptides.
Figure 4:
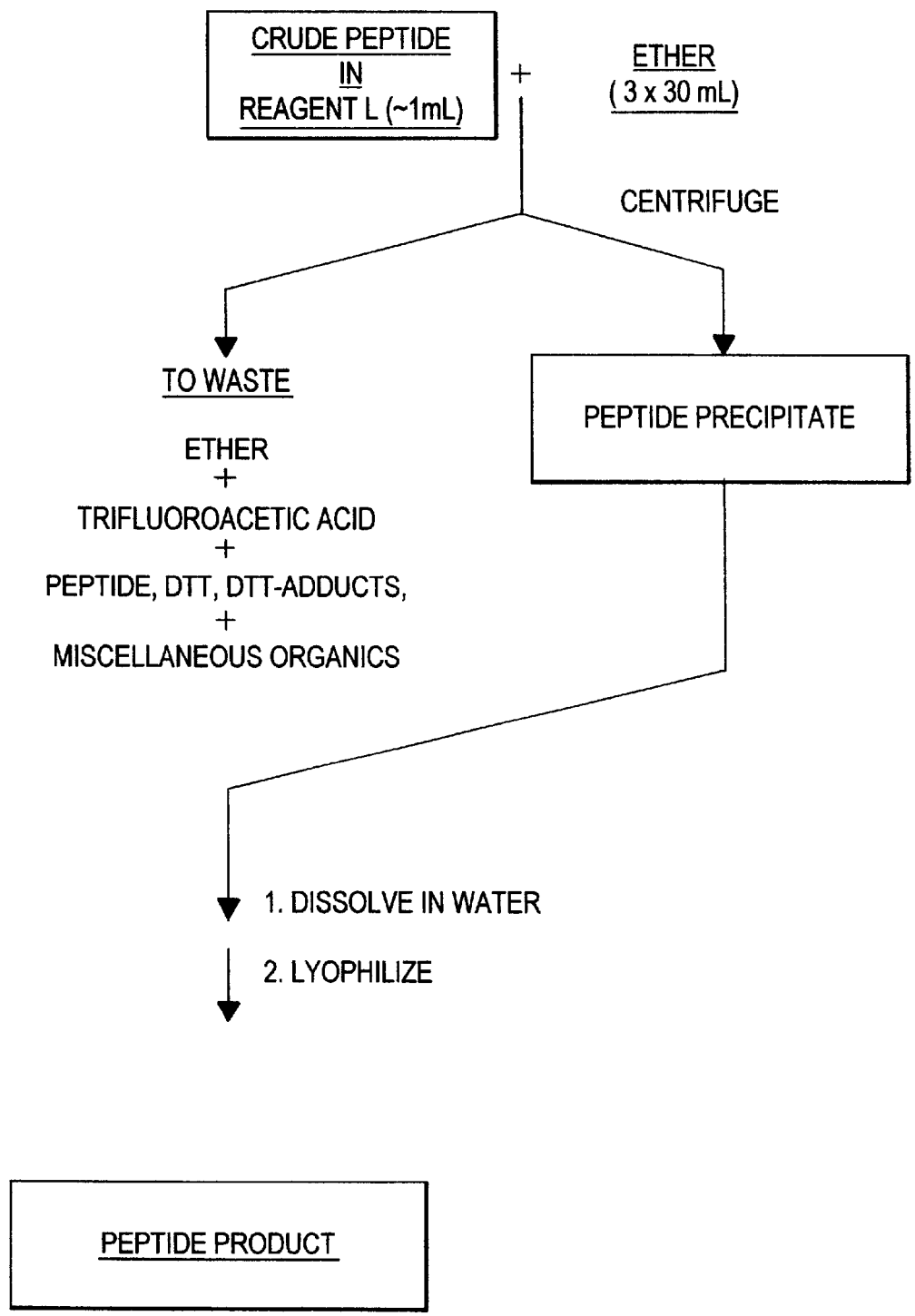
FIG. 4 schematically depicts a commonly used procedure using large amounts of diethyl or t-butylmethyl ether added directly to the Reagent K cocktail to cause the peptide to precipitate from the mixture.

As a point of reference, standard approaches to SPE were applied to purification of synthetic peptides as shown in FIG. 3. SPE approaches were studied with eight different peptide samples with varying physical properties and SPE elution characteristics. In these examples, the peptide and impurities were adsorbed onto the SPE sorbent and eluted with solvents of increasing solvent strength with the aim of selectively eluting the impurities. It was found that while 5% acetonitrile/water removed the thiol protecting compounds (dithiothreitol), stronger solvents (25% acetonitrile/water) eluted both peptide and other impurities. For this reason, a final liquid-liquid extraction with ether was necessary. It was determined that the standard approach SPE followed by a final liquid-liquid extraction step involved excessive sample handling steps which were awkward to apply when dealing with multiple samples and would be difficult to automate.
Advantages of the inventive Process in Peptide Synthesis Chemistry Synthetic peptides, prepared by solid phase synthesis by FMOC chemistry, are generally released from the synthesis resin by treatment with trifluoroacetic acid based cleavage and deprotection cocktails containing carbocation scavengers and reducing agents. These cocktails are conventionally known in the art as Reagents R, K, L, etc. Subsequently, the peptides are isolated from the components of the cleavage/deprotection mixture by well-known liquid-liquid extraction or trituration/precipitation methods. The most commonly used procedure, shown in FIG. 4, uses large amounts of diethyl or t-butylmethyl ether added directly to the Reagent K cocktail to cause the peptide to precipitate from the mixture. The impurities, scavengers, scavenger adducts, and organic by-products remain in the supernatant, which is discarded.

The ether precipitation method is widely accepted, commonly practiced, and applicable to nearly all peptides. However, some peptides do not precipitate but remain in solution. Also, application to small scale synthesis is problematic because handling and manipulations of milligram amounts of precipitate is difficult. The method requires centrifugation to separate the precipitate from the organic solvents and the use of highly flammable ether in a bench top centrifuge which, with its electric motor, presents a hazardous situation. Handling of flammable ether and corrosive trifluoroacetic acid solutions is dangerous and must be carried out in a well ventilated fume hood. Automatic instruments for ether precipitation and extraction have been reported but the method is impractical to automate because of the flammability of ether and the corrosive nature of trifluoroacetic acid. Simultaneous processing of multiple samples is limited or not practical due to the process requirements for multiple required steps, multiple centrifugations, and handling issues regarding corrosive reagents and flammable solvents. Typically, the ether precipitation method in peptide synthesis requires individual handling of a few samples at a time by trained technicians.

Application of the methods of the invention to synthetic peptide chemistry overcomes the disadvantages of the ether precipitation method, provides for convenience for multiple sample handling, and the process can be automated without difficulty.

EXAMPLE

The following example is intended to illustrate, without limitation, the invention. As shown in Table 1, three peptidyl-resins were synthesized and used to compare the new SPPE process to the standard ether precipitation process. These three peptides were prepared with 'standard' FMOC chemistries using Tentagel™ resins loaded at about 0.2 mmole/gm resin.

TABLE 1

| Sample No. | Sequence |
| --- | --- |
| 1 | H$_2$N—S Q E T F S D L W K L L P E N—Tentagel (Trt on W; Boc on K; Trt on N; Bu on S,T,S,D,E) |
| 2 | H$_2$N—C P D F H A M E L S G R W K Y-Tentagel (Trt on C; Trt on H; Pbf on R; Boc on K; Bu on D,E,S,Y) |
| 3 | H$_2$N—L L D G P G A E R S K E M P R—Tentagel (Pbf on R; Pbf on R; Bu on D,E,S,E; Boc on K) |

These peptidyl resins were chosen because of availability, purity, size of peptide, sensitive residues (Cys, Trp and Met), multiple and representative protecting groups, and the variable elution times of the cleaved and deprotected peptide from reverse phase HPLC.

Experimental Methods:

Peptidyl Resins: Peptidyl resins were obtained from Sigma-Genosys. They were prepared with standard FMOC procedures on Tentagel resins (Rapp Polymere) loaded at about 0.2 nmuole/gm with the C-terminal amino acid.

Reagent L Cocktail: Reagent L was prepared immediately before use and contained trifluoroacetic acid (88%), triisopropylsilane (2%), dithiothreitol (5%) and water (5%). All reagents were from Aldrich.

Cleavage and Deprotection. Peptidyl resins (100 mg) of Samples 1, 2 and 3 were allowed to stand with 750 ml of Reagent L for 90 min at RT. The Reagent L - sample was collected by filtration and the resin was washed with 250 ml of trifluoroacetic acid. The filtrate was diluted to 10 ml with water and frozen. This solution was used as a stock solution.

Solid phase columns: columns were prepared by transferring 0.5 gm of RP3 reverse phase sorbent (a 45-60 micron, macroporous polymeric support, Chemicus PIN RP3-4560) to a 6 ml plastic syringe with a porous frit at the bottom and at the top. The columns were prepared, prewashed and used with a Supelco 12-position Visiprep™ System. Columns were conditioned just prior to use by washing with acetonitrile (3×5 ml), acetonitrile:water 1:1 (3×5 ml) and trifluoroacetic acid:water 1:10 (4×5 ml).

Purification procedure: A 1-ml sample of the stock solution of peptide (previously described) was transferred to a prewashed column. The 1 ml sample was forced through the column by vacuum and the column was washed with trifluoroacetic acid:water 1:10 (3×5 ml). Columns were aspirated to dryness (2–3 min.) and dried under vacuum overnight in a desiccator. The removal of residual water was measured by weight loss of approximately 1.1 gm/column. The dried column was washed with cold (−20° C.) diethyl ether (3×3 ml). The columns were aspirated for 2–3 minutes after collection of the organic wash. Finally, the columns were washed with acetonitrile:water 1:3 (3×3 ml). These washings were collected and portions were analyzed by HPLC.

HPLC procedure: Samples were analyzed at 220 nm with a Waters 600 LC system using a 250 mm×4.5 mm Vydac™ column (p/n 218TP54, 5$\mu$) with a gradient of solvent A (water) to solvent B (acetonitrile). Both solvents were approximately 0.1% trifluoroacetic acid. Absorbances were adjusted and matched at 220 nm using the spectrophotometer and by addition of TFA as needed. The gradient was as below. Injections were made by an automatic sample injector (WISP) and, unless otherwise indicated, 50 $\mu$l was injected.

TABLE 2

| time | flow | A | B | Grad. |
|---|---|---|---|---|
| Init | 1.0 | 90 | 10 | * |
| 15 | 1.0 | 40 | 60 | 6 |
| 18 | 1.0 | 90 | 10 | 6 |
| 25 | 1.0 | 90 | 10 | 6 |
| 45 | 0.0 | 90 | 10 | 10 |

HPLC sample preparation: The first two (2×5 ml) trifluoroacetic acid:water 1:10 washes were collected and a 1 ml aliquot was stripped to dryness in the Speedvac. The residue was dissolved in 100 $\mu$l acetonitrile and 900 $\mu$l water was added. Ether washes of the columns were collected and dried by a stream of nitrogen. The residue was dissolved in 100 $\mu$l acetonitrile and 900 $\mu$l water was added. A 100 $\mu$l aliquot of the 25% acetonitrile wash (10 ml) was injected without dilution or modification. The "crude peptide" samples were prepared by diluting a 100 $\mu$l aliquot of the stock solution (described previously) with 900 $\mu$l water.

Data Analysis: EZChrom Elite™ software from Scientific Software, Inc. was used with the HPLC system for data handling and analysis.

Figure 5:
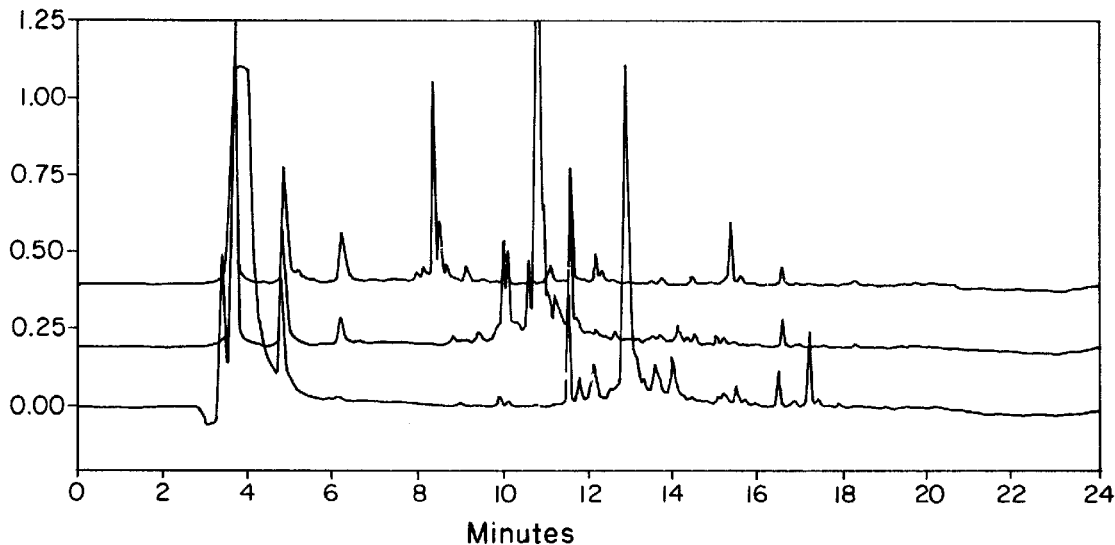
FIG. 5 depicts a superimposition of HPLC results of three crude samples after cleavage and deprotection with Reagent L and 10-fold dilution with water, as described in the Example.

Results and Discussion:

FIG. 5 superimposes the HPLC of the three crude samples so that common components can be discerned. It is interesting to note that there is a peak at about 11.5 minutes in all three samples, likely the t-butyl-DTT adduct. Peaks as 4.8 and 6.2 minutes in Sample 2 and 3 are common and one of these is likely DTT. A few peaks between 14 and 16 minutes, possibly trityl or Pbf by-products are common. An early peak at about 4 minutes was observed for Sample 1 and is probably due to salt and DMF which was added to the crude sample in an effort to solubilize the peptide.

Figure 6:
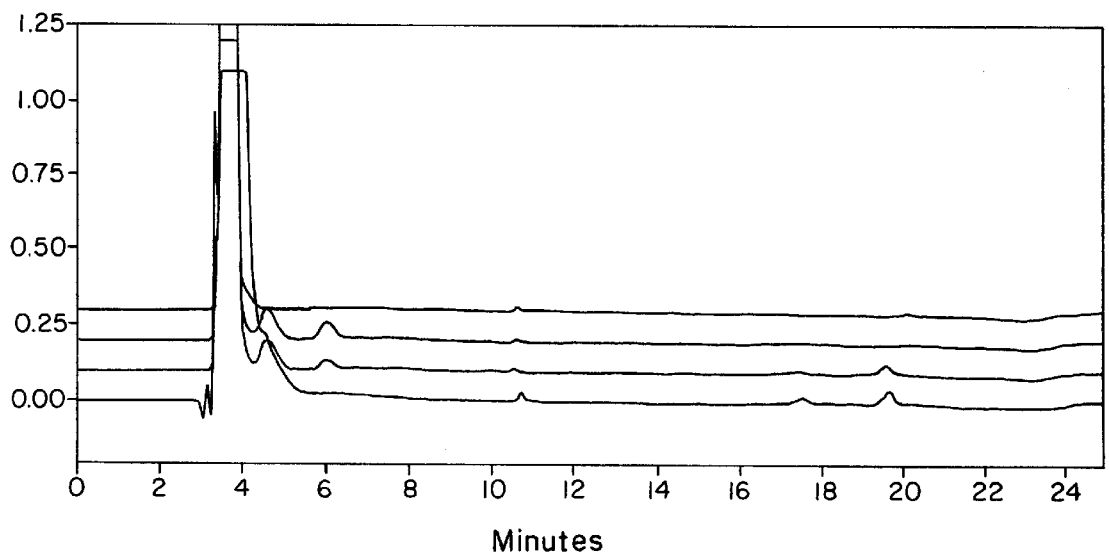
FIG. 6 depicts the HPLC analysis of the trifluoroacetic acid:water 1:9 washes described in the Example.

As seen in FIG. 6, the HPLC analysis of the trifluoroacetic acid:water 1:9 washes indicates that there is no peptide for any of the samples at this step of the procedure. For comparison, a blank sample was prepared in which solvents alone were processed through the SPPE column without peptide. Most of the peaks are at the front as expected and a small peak at about 11 minutes was observed in all samples.

Figure 7:
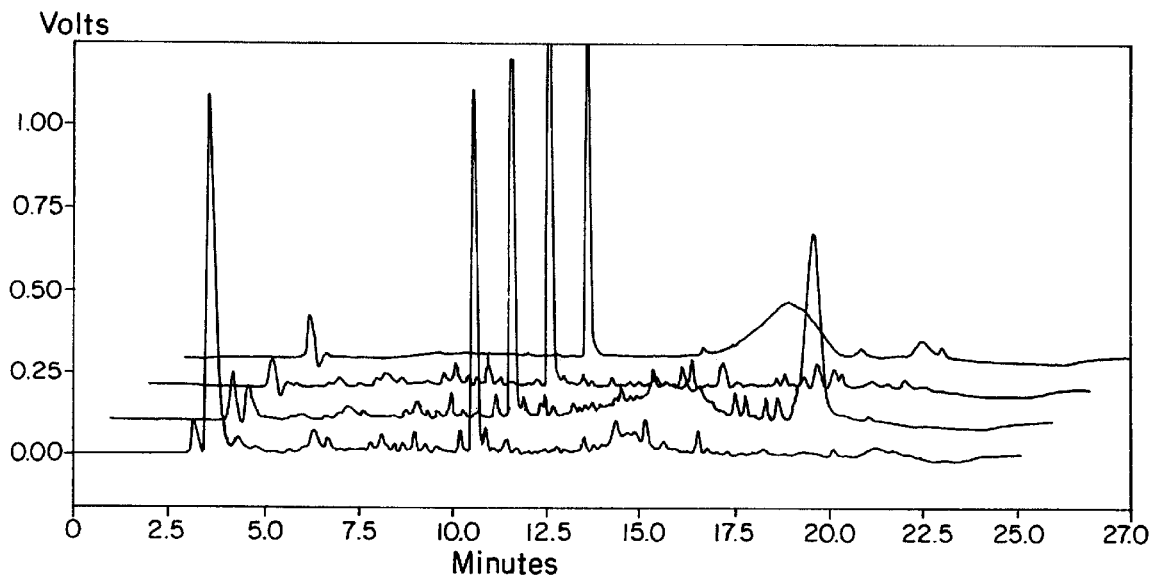
FIG. 7 depicts the HPLC analysis of the ether wash residue as described in the Example.

FIG. 7, the HPLC analysis of the ether wash residue, shows that there is no peptide for any of the samples of this step of the procedure. A number of small peaks were spread over the entire chromatogram for all samples except the blank. A large peak was observed at about 11 minutes in all samples including the blank and it is assumed that this unknown material elutes from the Oligo R3 sorbent. The early eluting peaks for sample 1 do not coincide with the other samples because this crude sample was treated with DMF and NaCl as described earlier.

Figure 8:
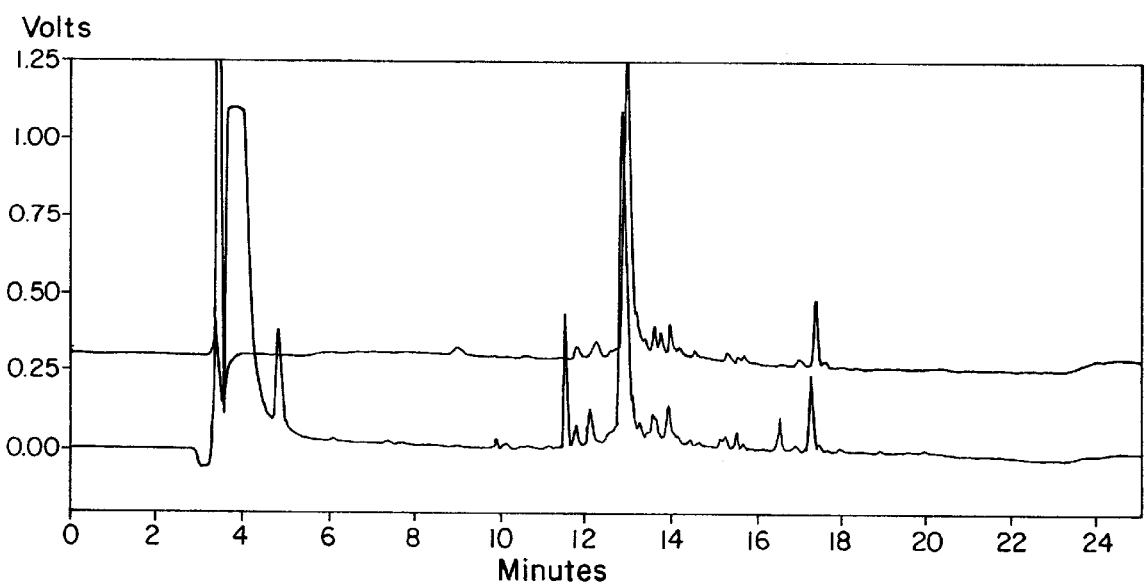
FIGS. 8, 9 and 10 are chromatograms for the three crude samples superimposed on the product after the complete SPPE protocol as described in the Example.
Figure 9:
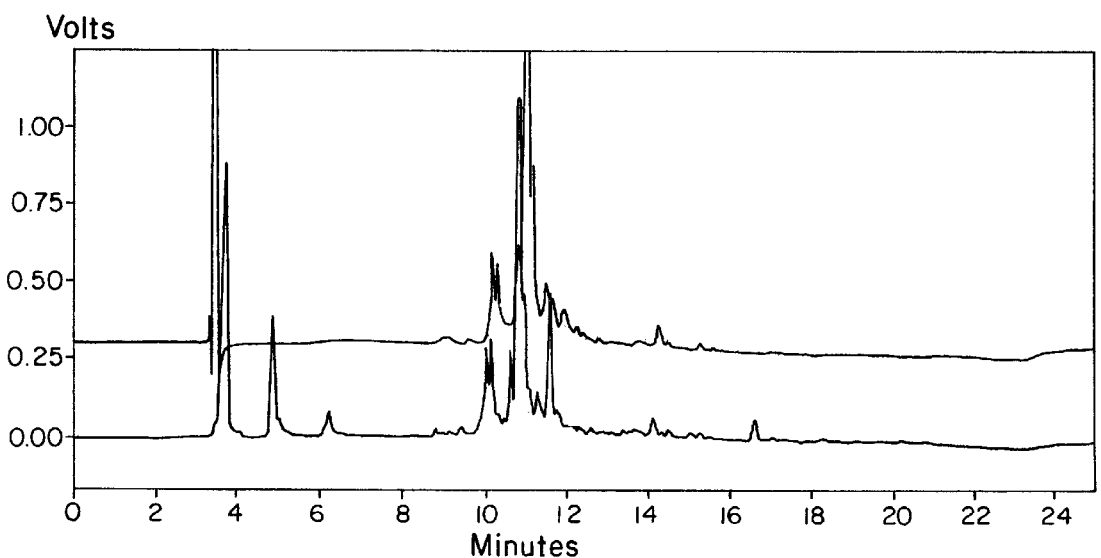
Figure 10:
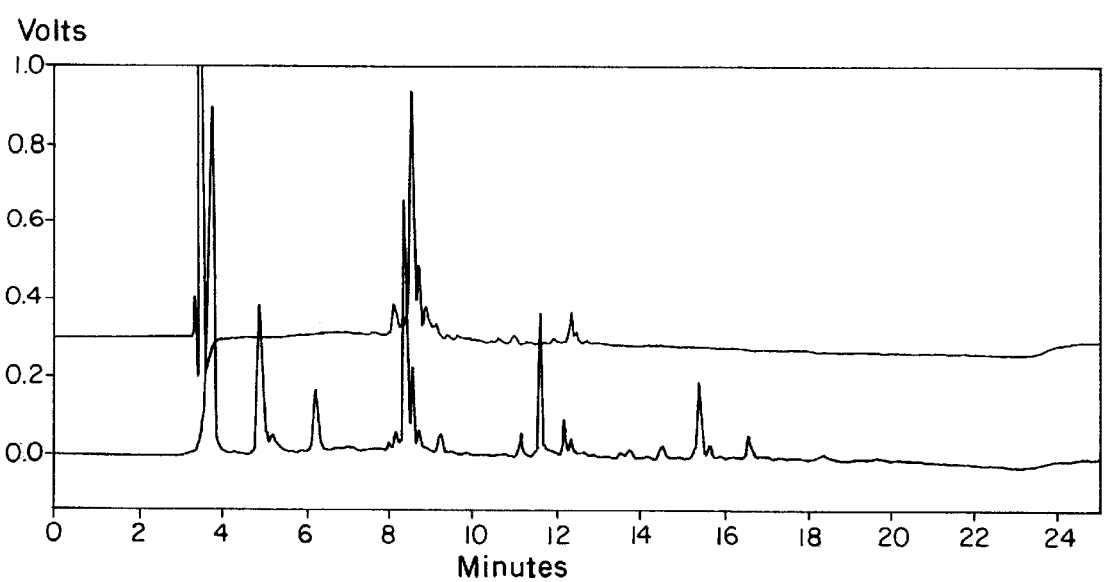
Figure 11:
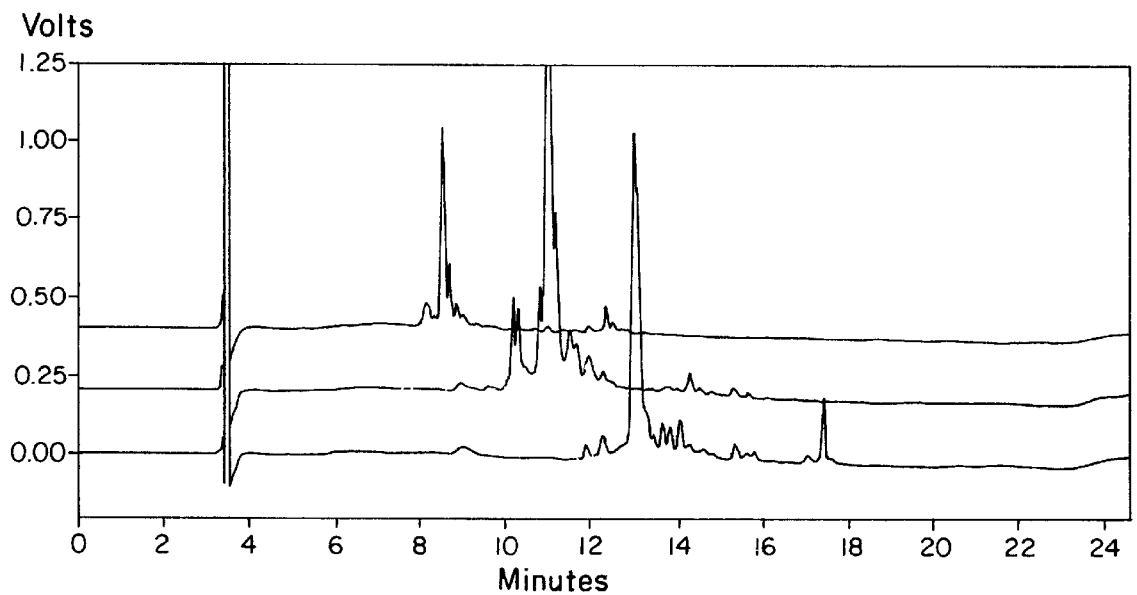
FIG. 11 is a compilation of all three products after the complete SPPE process.

FIGS. 8, 9 and 10 are chromatograms for the three crude samples superimposed on the product after the complete SPPE protocol. In all cases, the early eluting peaks and other common components noted above have been removed. FIG. 11 is a compilation of all three products after the complete SPPE process. Very few peaks are coincidental; therefore, the SPPE process yields primarily the 'compounds of interest' i.e., the peptide components from the crude peptide mixture samples. It should be noted that the isolated products shown in FIG. 11 are typical for peptide synthesis. Small peaks in the vicinity of the major peak are, most likely, deletion sequences which result from inefficiencies in the peptide synthesis chemistry. Shoulders on the major peak are either deletion sequences or oxidation products at Cys and Met residues. The very late eluting peak (about 17.5 minutes) in sample 1 was determined to be the product with the N-terminal FMOC group still attached, i.e., the result of inefficient removal of the FMOC moiety in the final synthesis step.

Figure 12:
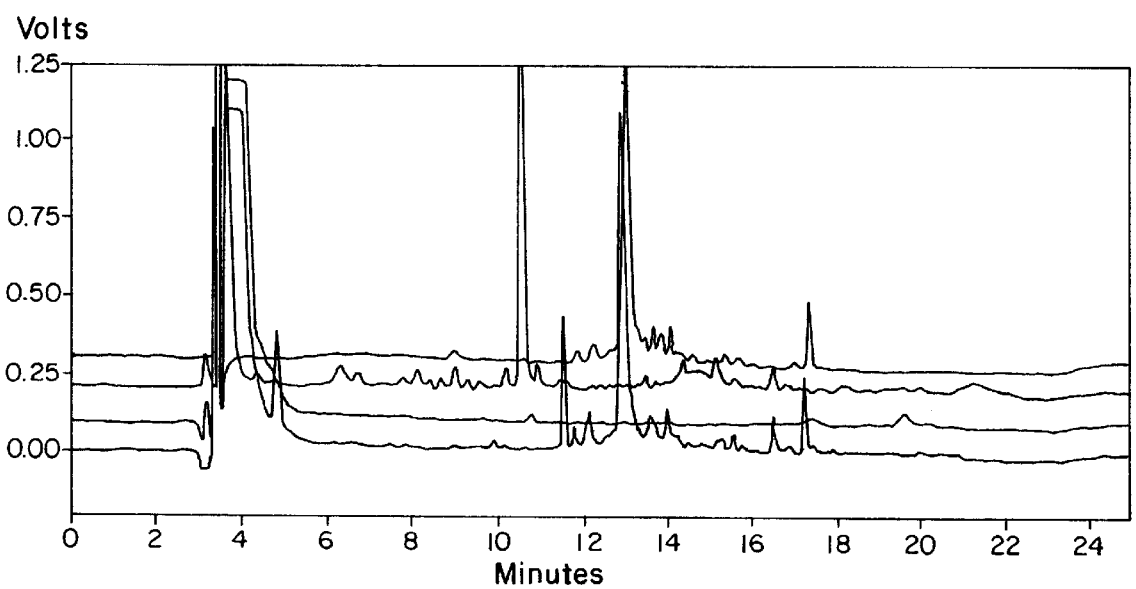
FIGS. 12, 13 and 14 are compilations of HPLC data for each sample and each step of the SPPE protocol as described in the Example.
Figure 13:
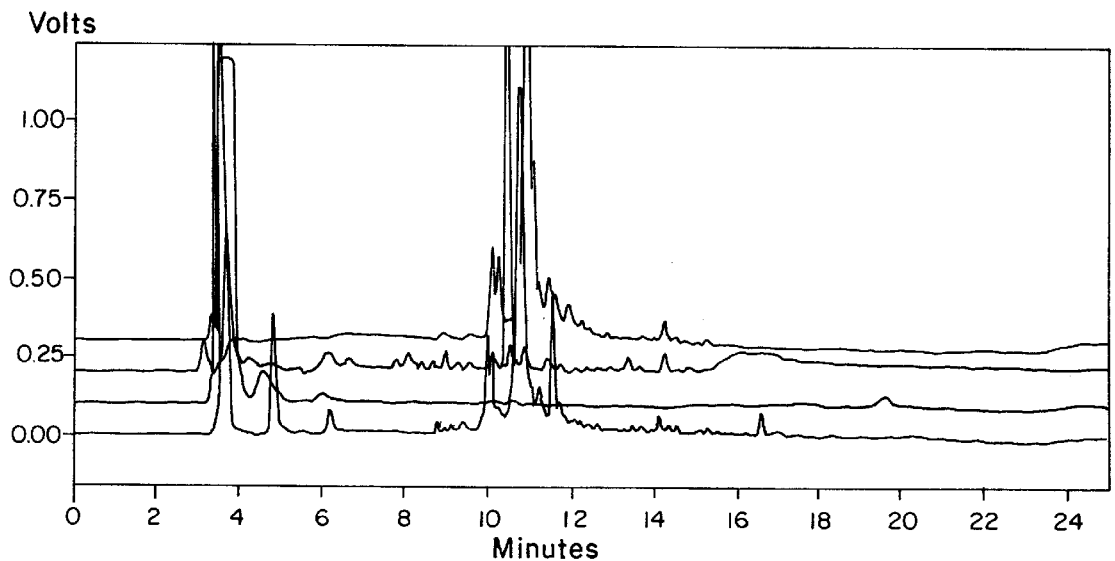
Figure 14:
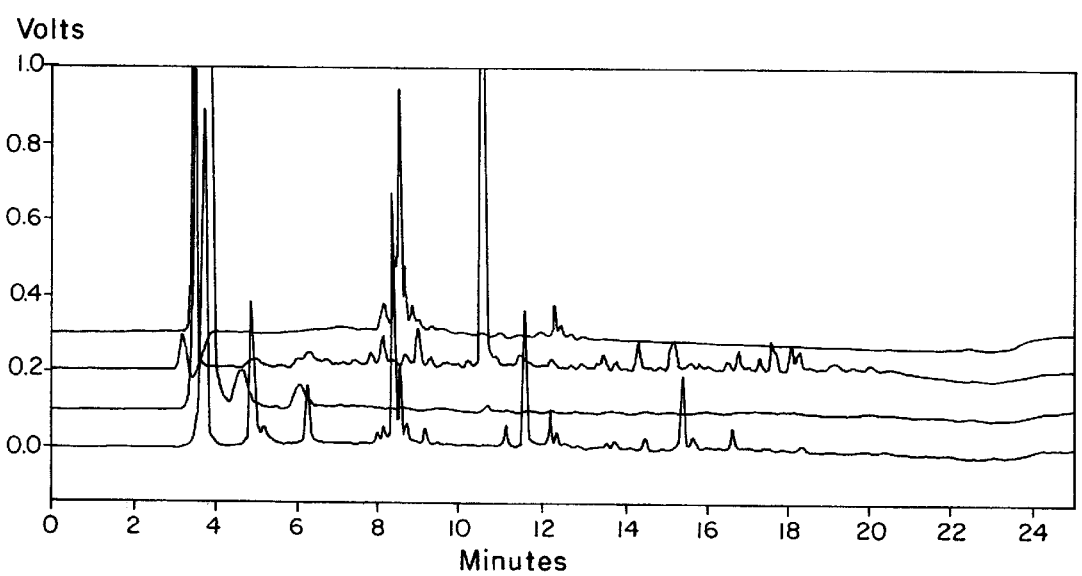

FIGS. 12, 13 and 14 are compilations of HPLC data for each sample and each step of the SPPE protocol. The chromatograms show the crude peptide, the 10% TFA wash, the ether wash, and the final product.

The area% of the major peaks in FIGS. 8, 9 and 10 are presented in the table below. In all cases, there is substantial improvement in the purity of the product. Integration of peaks was started at the 5-minute mark in the chromatograms so as to eliminate early solvent peaks from the calculations.

TABLE 3

| Sample | Area % Crude | Area % Product |
| --- | --- | --- |
| 1 | 49.9 | 59.6 |
| 2 | 44.0 | 53.7 |
| 3 | 25.6 | 50.6 |

Acidity of the aqueous wash step (i.e., the TFA:water 1:9), cold diethylether as the organic step, and prompt/rapid execution of the protocol (i.e. elimination of long exposure to air or suction on the Visiprep apparatus) are important details of the protocol which were determined to minimize oxidative side reactions that can affect the quality of the product. Finally, identical results were obtained using dichloromethane as the organic wash solvent.

Comparison of analytical data for the ether precipitation protocol product and the SPPE protocol product were virtually identical.

Analysis

The presently disclosed process, employs precipitation and thin film deposition to great advantage compared to traditional chromatography wherein great care is taken to prevent precipitation of the compounds of interest. Furthermore, in traditional chromatography drying the sorbent or the contents of a column must be avoided because it introduces bubbles into the fluid stream which complicate detection that usually relies on a consistent fluid stream for the detector flow cell. In fact, many chromatography columns are delivered wetted with a solvent, capped to prevent evaporation, and with instructions which suggest that drying the sorbent will negatively effect the plate count and performance of the column.

The presently disclosed process represents a significant improvement over existing methods for isolation of synthetic peptides and provides for novel approaches in separation methodology. Other R&D and industrial applications in nucleic acid chemistry, protein chemistry, and separation sciences. In addition, the process can be used for purification of combinatorially derived compound libraries which are the basis for drug discovery efforts at many pharmaceutical companies.

In application to peptide synthesis chemistry and in comparison with existing methods, the potential for automation and the capability for multiple sample handling are important features of the invention for isolation of synthetic peptide products after cleavage and deprotection.

Depending on the physical properties of the compounds of interest, the process of the invention is adaptable to ion exchange and normal phase sorbents, as well as reverse phase sorbents, by the choice of appropriate wash solvents.

Finally, the method can be applied to sample preparation, as well as analytical, preparative and process chromatography with monitoring by devices such as an ELS (evaporative light scattering) detector, which is not dependent on a flow cell with an uninterrupted fluid flow.

EQUIVALENTS

Those skilled in the art will recognize, or be able to ascertain using no more than routine experimentation, numerous equivalents to the specific procedures described herein. Such equivalents are considered to be within the scope of the present invention and are covered by the following claims. The contents of all references, issued patents, and published patent applications cited throughout this application are hereby incorporated by reference. The appropriate components, processes, and methods of those patents, applications and other documents may be selected for the present invention and embodiments thereof.

References 1. (a) P. D. McDonald and E. S. P Bouvier, Eds., Solid Phase Extraction Applications Guide and Bibliography: A Resource for Sample Preparation Methods Development, (Waters Corp., Milford, Mass., $6^{th}$ ed., 1995). (b) "Varian Sample Preparation Products," Varian Instruments (Harbor City, Calif., 1995) (c) "Bakerbond SPE Bibliography", J. T. Baker Inc. (Phillipsburg, N.J. 1995), (d) Tippins, B., Nature 334 (1988) 273–274. (e) Simpson, N., American Laboratory, August: 37–43 (1992). (f) Hawley, R., R&D Magazine, August: 51–54 (1991).

2. "Bulletin 910 Guide to Solid Phase Extraction", Supelco and Sigma-Aldrich (St. Louis, Mo. 1998).

3. (a) Fields, G. B. and Nobel, R. L., Int. J.Peptide Protein Res. 35 (1990) 161–214. (b) Atherton, E., and Sheppard, C. (1989) Solid Phase Peptide Synthesis: A practical Approach: IRL Press.

4. King, D., Fields, C., and Fields, G., Int.J.Peptide Protein Res. 36 (1990) 255–266.

5. Albericio, F., et.al., J.Org.Chem. 55 (1990) 3730–3743.

6. Duly, S., "Evaluation of a Low-Odor Reagent for Cleavage and Deprotection Following FMOC Solid-Phase Peptide Syntheis", (poster) The Fifteenth American Peptide Symposium (Nashville, Tenn.) June 1997.

7. (a) "Strategies in Peptide Synthesis", Perkin Elmer and Applied Biosystems (1990) 12–14. (b) Novabiochem Catalogue 94/95, p S39 (c) Van Wandelen, C., Zeikus, R., and Tsou, D., MilliGen/Biosearch Chemistry Update: December 1989. "Cleavage, Deprotection, and Isolation of Peptides after Fmoc Synthesis"

8. Zuckerman R., and Banville, S., Peptide Research 5 (1992) 169–174.

9. "Sequetag Column: Care and Use Manual", Waters Corp. (Milford, Mass. 1989).

10. Baxter, A.D., Genetic Engineering News, 19 (1999) 27.

What is claimed is:

1. A method for of isolating a biological analyte from a sample, comprising the steps of:
   a. precipitating said biological analyte onto a solid phase extraction media or device; and
   b. eluting said precipitated biological analyte off said solid phase extraction media or device;
   wherein said biological analyte is a protein, a peptide, a nucleic acid, or mixture thereof.

2. The method of claim 1, wherein said precipitation step comprises applying a liquid sample onto said solid phase extraction media or device followed by drying said solid phase extraction media or device.

3. The method of claim 1, wherein said drying step comprises applying a vacuum to said solid phase extraction media or device.

4. The method of claim 2, wherein said liquid sample is a cleavage/deprotection mixture containing synthetic peptides.

5. The method of claim 1, wherein said solid phase extraction media or device has been preconditioned with a solvent.

6. The method of claim 1, wherein said biological analyte comprises a post-cleavage mixture of synthetic peptides.

7. The method of claim 1, wherein said biological analyte is deposited as a thin film onto said solid phase extraction media or device.

8. The method of claim 1, wherein said solid phase extraction media or device is selected from the group consisting of a packed column of solid phase extraction particles, and a solid phase extraction membrane.

9. A method of claim 1, wherein said sample is a aqueous solvent.

10. A method of claim 1, wherein said sample is an organic solvent.

11. A method of claim 1, wherein said sample is a mixture of aqueous and organic solvent.

12. A method for of isolating a compound of interest from a sample, comprising the steps of;
   a. precipitating said compound of interest onto a solid phase extraction media or device; and
   b. eluting said precipitated compound of interest off said solid phase extraction media or device;
wherein said compound of interest is a protein, a peptide, a nucleic acid, or a mixture thereof.

13. A method of claim 1, wherein the biological analyze is a protein.

14. A method of claim 1, wherein the biological analyze is a peptide.

15. A method of claim 1, wherein the biological analyze is a mixture of protes and peptides.

16. A method of claim 2, wherein said precipitating step comprises adsorbing said biological analyre onto the solid phase extraction media or device and subsequently delivering a stream of gas or a washing solvent to precipitate the analyte onto the solid phase extraction media or device.

17. A method of claim 2, wherein said drying step comprises lypholization.

18. A method for isolating a peptide or a protein, comprising the steps of:
   a. adsorbing said peptide or protein in a first solvent onto a solid phase extraction media or device;
   b. delivering a second solvent to said solid phase extraction media or device to cause precipitation of a peptide or a protein and deposition as a thin film onto the solid phase extraction media or device; and
   c. elating the peptide or protein from the solid phase extraction media or device.

19. A method of claim 18, wherein the second solvent removes impurities and displaces the first solvent to cause precipitation of the peptide or protein.

20. A method of claim 18, wherein the first solvent is water and second solvent is diethyl ether, dichloromethane, acetonitile, acetone, or methanol.

* * * * *

UNITED STATES PATENT AND TRADEMARK OFFICE
CERTIFICATE OF CORRECTION

PATENT NO.    : 6,479,296 B1
DATED         : November 12, 2002
INVENTOR(S)   : Alex A. Bonner et al.

Page 1 of 1

It is certified that error appears in the above-identified patent and that said Letters Patent is hereby corrected as shown below:

<u>Column 9,</u>
Line 22, delete "analyze" and insert -- analyte --.
Line 24, delete "analyze" and insert -- analyte --.
Line 26, delete "analyze" and insert -- analyte --.

<u>Column 10,</u>
Line 2, delete "analyre" and insert -- analyte --.

Signed and Sealed this

Twenty-fifth Day of February, 2003

JAMES E. ROGAN
*Director of the United States Patent and Trademark Office*